United States Patent [19]

Schnettler et al.

[11] 4,410,540
[45] Oct. 18, 1983

[54] CARDIOTONIC 4-AROYLIMIDAZOLIDIN-2-ONES

[75] Inventors: Richard A. Schnettler; Richard C. Dage, both of Cincinnati, Ohio; J. Martin Grisar, Strasbourg, France

[73] Assignee: Merrell Dow Pharmaceuticals Inc., Cincinnati, Ohio

[21] Appl. No.: 317,963

[22] Filed: Nov. 4, 1981

[51] Int. Cl.³ .......................................... A61K 31/415
[52] U.S. Cl. ........................... 424/273 R; 424/248.5; 424/248.57; 424/250; 424/267; 544/139; 544/370; 546/210; 548/318; 548/321
[58] Field of Search .................. 424/267, 273 R, 250, 424/248.57, 248.5

[56] References Cited

U.S. PATENT DOCUMENTS 3,337,580 8/1967 Lunsford et al. .................. 548/321

OTHER PUBLICATIONS

Chemical Abstracts, 90:64361j (1979) [Endo, T., et al., JPN. Kokai Tokkyo Koho 78 52,422, 5/12/78].
Chemical Abstracts, 87:152201a (1977) [Miyoshi, M., et al., Japan, Kokai 77 46,074, 4/12/77].

Primary Examiner—Richard A. Schwartz
Attorney, Agent, or Firm—Stephen L. Nesbitt; Raymond A. McDonald; Gary D. Street

[57] ABSTRACT

This invention relates to aroyl-2-imidazolidinones of the following general structure which are useful as cardiotonics and antihypertensive agents

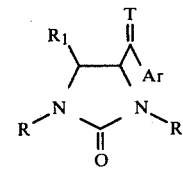

wherein Ar is furanyl, thienyl, 1H-pyrrolyl, or phenyl optionally substituted with one or two X groups; X is halogen, hydroxy, lower alkyl, lower alkoxy, lower alkylthio, lower alkylsulfoxide, lower alkylsulphone, trifluoromethyl, —$SO_2N(R_2)_2$, $NR_3R_4$, pyrrolidino, piperidino, morpholino, piperazino or N'-alkylpiperazino; R is hydrogen, lower alkyl, lower alkylcarbonyl or benzoyl; each of $R_1$, $R_2$, $R_3$ and $R_4$ is hydrogen or lower alkyl; T is an oxygen atom or a divalent sulfur atom; and the pharmaceutically acceptable salts thereof.

5 Claims, No Drawings

CARDIOTONIC 4-AROYLIMIDAZOLIDIN-2-ONES

FIELD OF THE INVENTION

This invention relates to 4-aroylimidazolidin-2-ones and their use as antihypertensives, cardiotonics and antithrombotics.

SUMMARY OF THE INVENTION

This invention is directed to pharmaceutically active 4-aroylimidazolidin-2-ones of general Formula 1

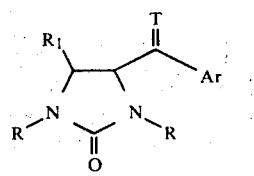

Formula 1 wherein Ar is furanyl, thienyl, 1H-pyrrolyl, phenyl, substituted phenyl substituted at the ortho, meta or para position with $X_1$, or disubstituted phenyl substituted at the ortho, meta or para position with $X_2$ and substituted at the meta or para position with $X_3$; $X_1$ is halogen, hydroxy, lower alkyl, lower alkoxy, lower alkylthio, lower alkylsulfoxide, lower alkylsulphone, trifluoromethyl, $-SO_2N(R_2)_2$, $NR_3R_4$, pyrrolidino, piperidino, morpholino, piperazino or N'-alkyl-piperazino; $X_2$ and $X_3$ are halogen, hydroxy, lower alkyl, lower alkoxy or when $X_2$ and $X_3$ are substituted on adjacent carbon atoms of the phenyl ring together they may form a methylenedioxy; R is hydrogen, lower alkyl, lower alkylcarbonyl or benzoyl; each of $R_1$, $R_2$, $R_3$ and $R_4$ is hydrogen or lower alkyl; T is an oxygen atom or a divalent sulfur atom; and the pharmaceutically acceptable salts thereof. These compounds are useful as antihypertensives, cardiotonics and antithrombotics.

DESCRIPTION OF THE PREFERRED EMBODIMENTS

As used herein, the term "lower alkyl" includes straight or branched-chain alkyl of from 1 to 4 carbon atoms such as methyl, ethyl, propyl, isopropyl, n-butyl and isobutyl.

As used herein, the term "lower alkoxy" includes straight or branched chain alkoxy of from 1 to 4 carbon atoms such as methoxy, ethoxy, n-propoxy, isopropoxy, n-butoxy and isobutoxy.

As used herein, the term "halogen" includes fluorine, chlorine, bromine or iodine.

As used herein, the term "halide" includes fluoride, chloride, bromide or iodide.

As used herein, the term "lower alkylthio" includes straight or branched chain alkylthio of from 1 to 4 carbon atoms such as methylthio, ethylthio, n-propylthio, isopropylthio, n-butylthio and isobutylthio.

As used herein, the term "methylenedioxy" is taken to mean methylenedioxy which may be substituted by one or two methyl groups, that is ethylenedioxy or isopropylidenedioxy.

As used herein, the term "benzoyl" is taken to mean a group of the formula, $-(CO)C_6H_5$.

As used herein, the term "lower alkylcarbonyl" is taken to mean a group of the structure

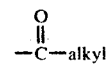

wherein the alkyl moiety is a straight or branched chain alkyl of from 1 to 4 carbon atoms such as methyl, ethyl, n-propyl, isopropyl, n-butyl and isobutyl.

As used herein, the term "N'-alkyl-piperazino" is taken to mean a group of the structure

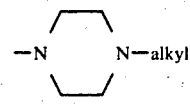

wherein the alkyl moiety is a straight or branched chain alkyl of from 1 to 4 carbon atoms such as methyl, ethyl, n-propyl, isopropyl, n-butyl and isobutyl.

As used herein, the term "furanyl" includes 2-furanyl and 3-furanyl.

As used herein, the term "thienyl" includes 2-thienyl and 3-thienyl.

As used herein, the term "pyrridyl" includes 2-pyrridyl, 3-pyrridyl and 4-pyrridyl.

As used herein, the term 1H-pyrrolyl includes 2-(1H-pyrrolyl) and 3-(1H-pyrrolyl).

As used herein, the term "lower alkyl sulfoxide" is taken to mean a group of the formula

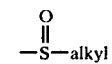

wherein the alkyl moiety is a straight or branched chain alkyl of from 1 to 4 carbon atoms such as methyl, ethyl, n-propyl, isopropyl, n-butyl and isobutyl.

As used herein, the term "lower alkyl sulfone" is taken to mean a group of the formula

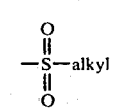

wherein the alkyl moiety is a straight or branched chain alkyl of from 1 to 4 carbon atoms such as methyl, ethyl, n-propyl, isopropyl, n-butyl and isobutyl.

The preferred compounds of this invention are those compounds of Formula 1 wherein R is hydrogen; T is an oxygen atom; and wherein $X_1$, $X_2$ and $X_3$ are halogen, lower alkyl, lower alkoxy, lower alkylthio or $X_2$ and $X_3$ together are methylenedioxy.

The more preferred compounds of this invention are those compounds of Formula 1 wherein T is an oxygen atom; R is hydrogen; and Ar is phenyl, monosubstituted phenyl or disubstituted phenyl wherein $X_1$, $X_2$ and $X_3$ are lower alkyl, lower alkoxy, lower alkylthio or $X_2$ and $X_3$ together are methylenedioxy.

The most preferred compounds of this invention are those compounds of Formula 1 wherein T is an oxygen atom; R is hydrogen; Ar is phenyl or monosubstituted phenyl; and $X_1$ is lower alkyl, lowr alkoxy or lower alkylthio.

As examples of compounds of general Formula 1 there may be mentioned the following:
4-benzoyl-5-methyl-2-imidazolidinone;
4-ethyl-5-(3-thienoyl)-2-imidazolidinone;

1,3-dimethyl-4-ethyl-5-(3,4-methylenedioxybenzoyl)-2-imidazolidinone;
4-(3-sulfonamidobenzoyl)-2-imidazolidinone;
1,3-diacetyl-4-[4-methyl(thiobenzoyl)]-2-imidazolidinone;
4-(2-methoxybenzoyl)-2-imidazolidinone;
4-(2-furanoyl)-5-isopropyl-2-imidazolidinone;
4-[4-dimethylamino(thiobenzoyl)]-2-imidazolidinone;
4-ethyl-5-(3-pyrrolidinobenzoyl)-2-imidazolidinone;
1,3-dibenzoyl-4-(4-methylpiperazinobenzoyl)-2-imidazolidinone;
4-[2,4-dibromo(thiobenzoyl)]-2-imidazolidinone;
4-[3,4-dimethyl(thiobenzoyl)]-5-methyl-2-imidazolidinone;
4-(2,4-dimethoxybenzoyl)-2-imidazolidinone;
4-ethyl-5-(3,4-methylenedioxybenzoyl)-2-imidazolidinone;
4-(2-pyrroloyl)-2-imidazolidinone;
4-(3-hydroxybenzoyl)-2-imidazolidinone;
4-(2,5-dichlorobenzoyl)-2-imidazolidinone;
4-butyl-5-(2,5-dihydroxybenzoyl)-2-imidazolidinone;
4-[2,5-dimethyl(thiobenzoyl)]-2-imidazolidinone; and
4-methyl-5-(4-morpholinobenzoyl)-2-imidazolidinone.

Those compounds of Formula 1 wherein R is hydrogen are acidic and may form pharmaceutically active salts of Formula 2

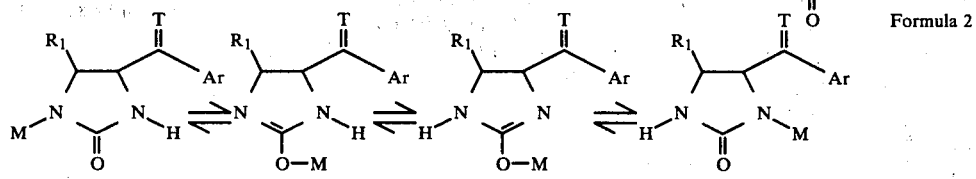

wherein Ar, T and $R_1$ are as defined in Formula 1, and M is a pharmaceutically acceptable alkali metal such as sodium or potassium; alkaline earth metal such as calcium or magnesium, transition metal such as zinc or iron; main group metal.

In general, the compounds of this invention are prepared by standard techniques analogously known in the art.

More specifically, the 4-aroyl-2-imidazolidinones of this invention wherein R is hydrogen and T is an oxygen atom may be prepared by reacting an appropriate imidazolidine carboxylic acid of formula

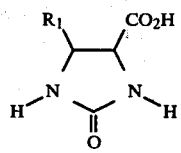

wherein $R_1$ is as defined in Formula 1 with an appropriate aromatic compound, that is, furan, thiophene, pyrrol, benzene or substituted benzene, and polyphosphoric acid (PPA). This reaction is performed with or without added solvent, by mixing about 1 molar equivalent of the appropriate imidazolidine carboxylic acid with about 1 molar equivalent to about 10 molar equivalents, preferably about 2 molar equivalents of PPA. About 1 molar equivalent to about 10 molar equivalents, preferably about 1.1 molar equivalents of the appropriate aromatic compound is added, preferably dropwise, to the mixture of imidazolidine carboxylic acid, PPA and the reaction is allowed to proceed for about ½ hour to about 24 hours, preferably about 1 hour depending on the reactants, the solvent, if any, and the temperature which can be from about 0° C. to about 125° C. preferably about 50° to 100° C., most preferably about 80° C. The resulting aroylimidazolidin-2-one may be isolated from the reaction mixture by any suitable art-known procedure, preferably by quenching the reaction mixture with ice water and subsequently removing the product by filtration or solvent extraction.

Although this reaction is preferably performed without added solvent, if solvent is desired, xylene is preferred. Other suitable solvents are any nonreactive solvents, for example, petroleum ethers; chlorinated hydrocarbons such as chloroform, methylene chloride or carbon tetrachloride; carbon disulfide; or ethereal solvents such as diethylether, tetrahydrofuran or p-dioxan.

Alternatively, the 4-aroyl-2-imidazolidinones of this invention wherein R is hydrogen or lower alkylcarbonyl and T is an oxygen atom may be prepared by reacting an appropriate imidazolidine acid halide of formula 4

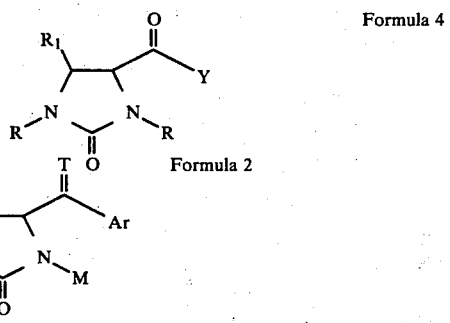

Formula 4 wherein R is lower alkylcarbonyl, Y is bromine, iodine or preferably chlorine, and $R_1$ is as defined in Formula 1 with an appropriate aromatic compound, that is, furan, thiophene, pyrrol, benzene or substituted benzene and a Lewis acid catalyst. This reaction is performed by mixing a suitable solvent and about 1 molar equivalent of the appropriate imidazolidine acid halide with about 1 molar equivalent to about 10 molar equivalents, preferably about 2 molar equivalents, of a Lewis acid catalyst. About 1 to about 10 molar equivalents, preferably about 1.1 molar equivalents of the appropriate aromatic compound is added, preferably dropwise, to the mixture of imidazolidine acid halide, Lewis acid catalyst and solvent. The reaction is allowed to proceed for about ½ hour to about 24 hours, preferably about 1 hour depending on the reactants, the solvent and the temperature which can be from about 0° C. to about 125° C., preferably about 50° to 100° C. The resulting aroylimidazolidin-2-one may be isolated from the reaction mixture by any suitable art-known procedure, preferably by quenching the reaction mixture with ice water and subsequently removing the product by filtration or solvent extraction.

If compounds of Formula 1 wherein R is hydrogen are desired, they may be prepared from the corresponding 4-aroyl-2-imidazolidinone prepared above wherein R is lower alkylcarbonyl by acid hydrolysis via procedures generally known in the art. Suitable acids for this reaction are hydrochloric acid or sulfuric acid.

When desired, compounds of general Formula 1 wherein T is a divalent sulfur atom may be prepared from the corresponding compound wherein T is an oxygen atom by treatment with $P_2S_5$. This reaction is performed by mixing about 1 molar equivalent of the appropriate imidazolidin-2-one wherein T is an oxygen atom with about 1 molar equivalent to about 10 molar equivalents, preferably about 1.1 molar equivalents, of $P_2S_5$ and a solvent. The reaction is allowed to proceed for about ½ to about 10 hours, preferably about 1 hour, depending on the reactant, the solvent and the temperature which can be from about 25° to about 125° C., preferably about 100° C. The resulting 2-imidazolidinone, wherein T is a divalent sulfur atom, may be isolated from the reaction mixture by any suitable are-known procedure such as by quenching the reaction mixture with ice water and subsequently removing the product by filtration or extraction and solvent removal.

Suitable solvents for use in the above-described sulfuration reaction are any non-reactive solvent, for example, petroleum ethers; chlorinated hydrocarbons such as chloroform, methylene chloride, carbon tetrachloride or ethylene dichloride; carbon disulfide; ethereal solvents such as diethyl ether, tetrahydrofuran or p-dioxan; alcoholic solvents such as methanol, ethanol, t-butanol or ethylene glycol; and aromatic solvents such as p-xylene or preferably toluene.

When desired, one or both of the nitrogen atoms of the 2-imidazolidinone ring may be substituted with an alkyl group by any art-known procedure. Such methods include reacting the appropriate N-unsubstituted 2-imidazolidinone of this invention with a base and an alkylating agent in the presence of an unreactive solvent. Suitable bases for this reaction can be, for example, a hydride such as sodium hydride or calcium hydride; a carbonate or bicarbonate such as sodium carbonate or sodium bicarbonate; a phenoxide such as sodium phenoxide; an alkoxide such as sodium ethoxide; or preferably a hydroxide such as sodium hydroxide. Suitable alkylating agents for this reaction are, for example, an alkyl halide such as methyl chloride, methyl bromide, or methyl iodide; or a dialkylsulfate such as dimethylsulfate. Suitable unreactive solvents are, for example, petroleum ethers; chlorinated hydrocarbons such as carbon tetrachloride, chloroform, or methylene chloride; chlorinated aromatics such as 1,2,4-trichlorobenzene, o-dichlorobenzene, or chlorobenzene; carbon disulfide; nitrobenzene; ethereal solvents such as diethyl ether, tetrahydrofuran or p-dioxan; aromatic solvents such as benzene, toluene, or xylene; or preferably the polar aprotic solvents such as dimethylformamide (DMF) or dimethylsulfoxide (DMSO). The reaction is allowed to proceed from about 1 minute to about 1 hour and the temperature may be from about 0° C. to about 100° C., preferably about 25° C. When it is desired that only one of the 2-imidazolidinone nitrogen atoms be substituted with an alkyl group, the appropriate imidazolidin-2-one is reacted with from about 1 molar equivalent to about 10 molar equivalents of a base, preferably about 1 molar equivalent and with about 1 molar equivalent of an alkylating agent. Utilizing this procedure, both possible monoalkylated nitrogen isomers result. These isomers are separable by conventional art-known procedures such as fractional crystallization, fractional distillation, or chromatography. When it is desired that both nitrogen atoms of the 2-imidazolidinone ring be alkyl substituted, the appropriate imidazolidin-2-one is reacted with from about 2 molar equivalents to about 10 molar equivalents of a base, preferably about 2 molar equivalents and from about 2 molar equivalents to about 10 molar equivalents of an alkylating agent, preferably about 2 molar equivalents. Finally, any reactive substituents on the aroyl rings, if present, may become alkylated concurrently. That is, the following X groups, $X=OH$, $-NHR_3$, $SO_2NH_2$ and unsubstituted piperazino, are alkylated under identical reaction conditions. If desired, the alkylation of the aroyl ring substituents may be avoided by the use of suitable protecting groups well-known in the art, for example, $X=OH$ or $-NHR_3$ may be benzylated and later deblocked by hydrogenolysis.

When desired, the nitrogen atoms of the 2-imidazolidinone ring may be substituted with an alkylcarbonyl or benzoyl group by any suitable art-known procedure. Such methods include reacting the N-unsubstituted imidazolidin-2-one of this invention with an acyl halide, preferably an acyl chloride such as acetyl chloride, n-propanoyl chloride, isopropanoyl chloride or benzoyl chloride. Normally, acylation reactions utilizing acyl halides employ an acid sponge such as triethylamine or pyridine to remove any hydrohalide as it is formed. Furthermore, the corresponding free acid or acid anhydride may be employed instead of the acyl halides. Acylation reactions are generally run without added solvent but may be performed using any nonreactive solvent, for example, petroleum ethers; chlorinated hydrocarbons such as chloroform, methylene chloride or carbon tetrachloride; carbon disulfide; ethereal solvents, such as diethylether, tetrahydrofuran or p-dioxan or aromatic solvents such as benzene, toluene or xylene. The reactions are allowed to proceed for about 1 minute to about 100 hours, preferably from about 1 hour to about 10 hours and the temperature may be from about $-78°$ to about 150° C., preferably from 0° to 100° C. Finally, any reactive substituents on the aroyl rings, if present, will become acylated concurrently. That is, the following X groups, $X=OH$, $-NHR_3$, $-SO_2NH_2$ and unsubstituted piperazino, are acylated under identical reaction conditions. If desired, the acylation of the benzoyl ring substituents may be avoided by the use of suitable protecting groups well-known in the art, for example $X=OH$ or $-NHR_3$ may be benzylated and later deblocked by hydrogenolysis.

The alkali metal, alkaline earth metal, transition metal, main group metal, ammonium or organic ammonium salts of the imidazolidin-2-ones of this invention may be prepared from a corresponding metal salt for example an alkoxide, such as sodium methoxide or sodium ethoxide or a hydroxide, such as sodium hydroxide. These reactions may be performed with or without a solvent. Suitable solvents are, for example, lower alcohols, such as methanol, ethanol, isopropanol, n-propanol or n-butanol; aromatic solvents, such as benzene, toluene or xylene; ethereal solvents, such as diethyl ether, tetrahydrofuran or p-dioxan; and halogenated hydrocarbon solvents, such as chloroform, methylene chloride or carbon tetrachloride. The imidazolidin-2-one and base are allowed to react for about 1 minute to about 24 hours depending on the reactants and the temperature which can be from about $-78°$ to about 150° C., preferably from about 0° to about 25° C.

The starting materials of Formula 3 may be prepared by any suitable art-known procedure. One such suitable procedure, *Helv. Chim. Acta* 9, 301 (1926), involves reacting a protected α-amino-β-carboxamido-carboxylic acid of formula 5

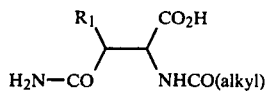

Formula 5 wherein $R_1$ is as defined above in Formula 1, with an oxychloride salt such as barium oxychloride and base such as sodium hydroxide. Acid hydrolysis yields the 2-imidazolidone-4-carboxylic acids.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic. In many respects these compounds possess digitalis-like action. The compounds of general Formula 1 may also be used in the treatment of hypertension including primary or essential hypertension, hormonally induced hypertension, renal hypertension and chemically induced hypertension.

The utility of Formula 1 compounds as antihypertensives may be determined by administering the test compound (50 mg/kg p.o.) to 6 spontaneously hypertensive rats (having a systolic blood pressure greater than 150 mm Hg) at 50 mg/5 ml/kg using 0.5% methylcellulose as a suspending vehicle. A control group of 6 spontaneously hypertensive rats receive 5 ml/kg of 0.5% methylcellulose. Caudal artery blood pressure is recorded via a photocell transducer placed over the tail just behind the pressure cuff. Three readings of approximately 2 minutes are made 1, 2, 3, 4 and 24 hours after dosing. A compound in this test is considered active is the mean fall in blood pressure is significantly ($p<0.05$) greater than control for at least one of the 1, 2, 3, 4 or 24 hour post-drug time periods.

The utility of Formula 1 compunds as cardiotonics may be determined by administering the test compound (1-10 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular); introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. The aorta and vena cava are connected to increase the venous return to the heart or the heart is vascularly isolated from the rest of the circulatory system. Heart failure is induced by administering sodium pentobarbitol (20-40 mg/kg injection by a constant infusion of 0.25 mg/kg/min) or propranalol hydrochloride (4 mg/kg injection followed by a constant infusion of 0.18 mg/kg/min) or by administering sodium pentobarbitol into the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is intravenously or intramuscularly. The amount of compound administered will vary with the severity of the hypertension or cardiac failure and the mode of administration.

For oral administration the antihypertensively effective amount of compound is from about 0.01 mg/kg (milligrams per kilograms) of patient body weight per day to about 500 mg/kg of patient body weight per day and preferably from about 1.0 mg/kg of patient body weight per day to about 50 mg/kg of patient body weight per day.

For parenteral administration the antihypertensively effective amount of compound is from about 0.01 mg/kg of patient body weight per day up to about 150 mg/kg of patient body weight per day and preferably from about 0.1 mg/kg of patient body weight per day up to about 10.0 mg/kg of patient body weight per day.

For oral or parenteral administration the cardiotonically effective amount of compound is from about 0.01 mg/kg of patient body weight per day up to about 500 mg/kg of patient body weight per day and preferably from about 0.1 mg/kg of patient body weight per day up to about 50.0 mg/kg of patient body weight per day.

For oral administration a unit dosage may contain, for example, from 1 to 500 mg of the active ingredient. For parenteral administration a unit dosage may contain, for example, from 1 to 50 mg of the active ingredient. Repetitive daily administration of the compounds may be desired and will vary with the condition of the patient and the mode of administration.

As used herein the term patient is taken to mean a warm blooded animal, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatine type containing, for example, lubricants and inert fillers, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animals, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicons, for example, Silastic, silicone rubber manufactured by the Dow-Corning Corporation.

The following are illustrative examples of the preparation and use of the compounds of this invention.

EXAMPLE 1

4-(3,4-Dimethoxybenzoyl)-5-ethyl-2-imidazolidinone

In 100 g PPA are suspended 15.8 g 4-ethyl-2-oxoimidazolidine-5-carboxylic acid and 13.8 g 1,2-dimethoxybenzene. The mixture is rapidly stirred and heated for 5 hours at 100° C. The reaction mixture is quenched with water and the product separates as a solid. The solid is collected and washed with water and dried. Purification is effected by chromatography over silica gel.

EXAMPLE 2

4-Isopropyl-5-benzoyl-2-imidazolidinone

Following the procedure of Example 1 but substituting 4-isopropyl-2-oxo-imidazolidine-5-carboxylic acid for 4-ethyl-2-oxo-imidazolidine-5-carboxylic acid and substituting benzene for 1,2-dimethoxybenzene gives the title compound.

EXAMPLE 3

4-Ethyl-5-(4-methoxybenzoyl)-2-imidazolidinone

Following the procedure of Example 1 but substituting methoxybenzene for 1,2-dimethoxybenzene, gives the title compound.

EXAMPLE 4

5-Propyl-4-furoyl-2-imidazolidinone

In 10 g PPA are placed 1.72 g n-propyl-2-oxoimidazolidine-5-carboxylic acid and 0.68 g furan. The mixture is heated and stirred at 80° C. for 10 hours, cooled and quenched with water. Extraction with chloroform followed by evaporation of solvent gives the title compound.

EXAMPLE 5

4-Propyl-5-(4-benzyloxybenzoyl)-2-imidazolidinone

Following the procedure of Example 4 but substituting benzyloxybenzene for further gives the title compound.

EXAMPLE 6

5-Ethyl-4-(4-fluorobenzoyl)-2-imidazolidinone

In 100 g PPA are suspended 15.8 g 4-ethyl-2-oxoimidazolidine-5-carboxylic acid and 10 g fluorobenzene. The mixture is heated to 100° C. for 10 hours with rapid stirring and poured into water. The product separates and is collected.

EXAMPLE 7

5-Ethyl-4-(4-chlorobenzoyl)-2-imidazolidinone

Following the procedure of Example 6 but substituting chlorobenzene for fluorobenzene gives the title compound.

EXAMPLE 8

4-Ethyl-5-[4-(1-piperidinyl)benzoyl]-2-imidazolidinone

A suspension of 10 g of 5-ethyl-4-(4-fluorobenzoyl)-2-imidazolidinone in 30 ml piperidine is stirred at reflux for 24 hours. Excess piperidine is evaporated under reduced pressure and the residue is purified by crystallization from alcohol.

EXAMPLE 9

1,3-Diethyl-5-methyl-4-(4-chlorobenzoyl)-2-imidazolidinone

In 100 ml DMF is placed 24.95 g 5-methyl-4-(4-chlorobenzoyl)-2-imidazolidinone and 4,8 g sodium hydride. To the well stirred mixture is added 31 g ethyl iodide. The mixture is stirred and heated at 80° C. for 2 hours, cooled and quenched with water. Extraction with ether affords the title compound.

EXAMPLE 10

4-Isopropyl-5-(phenylthioxomethyl)-2-imidazolidinone

To a stirred mixture of 10 g of 4-isopropyl-5-benzoyl-2-imidazolidone in 100 ml toluene is added 10 g phosphorus pentasulfide. The mixture is stirred, refluxed for 24 hours and the solvent is evaporated. The residue is purified by crystallization to give the title compound.

EXAMPLE 11

1,3-Diacetyl-4-ethyl-5-(4-methoxybenzoyl)-2-imidazolidinone

A solution of 10 g of 4-ethyl-5-(4-methoxybenzoyl)-2-imidazolidinone in 100 ml acetic anhydride is stirred at reflux for 5 hours after which the excess solvent is evaporated. The residue is purified by chromatography.

EXAMPLE 12

1,3-Dimethyl-4-propyl-5-(4-hydroxybenzoyl)-2-imidazolidinone

A solution of 33.8 g 4-propyl-5-(4-benzyloxybenzoyl)-2-imidazolidinone in 150 ml DMF is treated with 4.8 g sodium hydride. The solution is then treated with 28.4 g methyl iodide and is heated to 100° C. for 5 hours. The reaction solution is treated with water and extracted with ether. Evaporation of solvent affords 1,3-dimethyl-4-propyl-5-(4-benzyloxybenzoyl)-2-imidazolidinone which is purified by crystallization from alcohol.

1,3-dimethyl-4-propyl-5-(4-benzyloxybenzoyl)-2-imidazolidinone (10 g) is dissolved in 100 ml ethanol and the reaction flask charged with 100 mg 10% pallidium on charcoal. The mixture is hydrogenated at atmospheric pressure until 1 equivalent of hydrogen is consumed. After filtration and evaporation of solvent the title compound is obtained.

EXAMPLE 13

Preparation of a Tablet Formulation

|  | Per Tablet |
|---|---|
| (a) 4-(3,4-dimethoxybenzoyl)-5-ethyl-2-imidazolidinone | 100 mg |
| (b) Cornstarch | 15 mg |
| (c) Lactose | 35.5 mg |
| (d) Magnesium stearate | 1.5 mg |

EXAMPLE 14

Preparation of a Parenteral Formulation

| (a) 4-ethyl-5-(4-methoxybenzoyl)-2-imidazolidinone | 1.000 g |
|---|---|
| (b) Polyoxyethylene sorbitan monooleate | 2.000 g |
| (c) Sodium chloride | 0.128 g |
| (d) Water for injection qs ad | 20.0000 ml |

We claim:

1. A method for the treatment of a condition requiring the strengthening of heart action in a patient in need thereof which comprises administering to said patient a cardiotonically effective amount of a compound of the structure

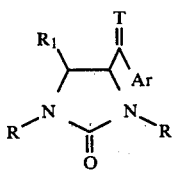

wherein Ar is furanyl, thienyl, 1H-pyrrolyl, phenyl, monosubstituted phenyl substituted at the ortho, meta or para position with $X_1$, or disubstituted phenyl substituted at the ortho, meta or para position with $X_2$ and substituted at the meta or para position with $X_3$; $X_1$ is halogen, hydroxy, lower alkyl, lower alkoxy, lower alkylthio, lower alkylsulfoxide, lower alkylsulfone, trifluoromethyl, $-SO_2N(R_2)_2$, $NR_3R_4$, pyrrolidino, piperidino, morpholino, piperazino or N'-alkylpiperazino; $X_2$ and $X_3$ are each halogen, hydroxy, lower alkyl, lower alkoxy or when $X_2$ and $X_3$ are substituted on adjacent carbon atoms of the phenyl ring together they may form a methylenedioxy; R is hydrogen, lower alkyl, lower alkylcarbonyl, or benzoyl; each of $R_1$, $R_2$, $R_3$ and $R_4$ is hydrogen or lower alkyl; T is an oxygen atom or a divalent sulfur atom; or a pharmaceutically acceptable salt thereof.

2. A method of claim 1 wherein R is hydrogen and T is an oxygen atom.

3. A method of claim 2 wherein $X_1$ is halogen, lower alkyl, lower alkoxy or lower alkylthio.

4. A method of claim 2 wherein $X_2$ and $X_3$ are each halogen, lower alkyl, lower alkoxy, lower alkylthio or when $X_2$ and $X_3$ are substituted on adjacent carbon atoms together they may form a methylenedioxy.

5. A method of claim 2 wherein Ar is phenyl or monosubstituted phenyl substituted at the ortho, meta or para position with methyl, ethyl, methoxy, ethoxy or methylthio.

* * * * *